United States Patent [19]

Tanaka

[11] Patent Number: 5,320,106
[45] Date of Patent: Jun. 14, 1994

[54] INTRACAVITARY DIAGNOSING APPARATUS EMPLOYING ULTRASOUND

[75] Inventor: Toshizumi Tanaka, Omiya, Japan

[73] Assignee: Fuji Photo Optical Co., Ltd., Saitama, Japan

[21] Appl. No.: 19,255

[22] Filed: Feb. 18, 1993

[30] Foreign Application Priority Data

Feb. 20, 1992 [JP] Japan .................... 4-070351

[51] Int. Cl.⁵ .............................. A61B 8/12
[52] U.S. Cl. ..................... 128/662.06; 128/663.01
[58] Field of Search ............... 128/662.05, 662.06, 128/663.01, 4

[56] References Cited

U.S. PATENT DOCUMENTS 4,408,612 10/1983 Utsugi ..................... 128/662.06
5,000,185 3/1991 Yock ....................... 128/662.06
5,029,588 7/1991 Yock et al. ............... 128/662.06
5,203,338 4/1993 Jang ....................... 128/662.06

Primary Examiner—William E. Kamm
Assistant Examiner—George Manuel
Attorney, Agent, or Firm—Townsend & Banta

[57] ABSTRACT

An intracavitary diagnosing apparatus employs an ultrasonic probe whose focused range can be moved. In the ultrasonic probe are disposed an ultrasonic transducer and an ultrasonic mirror for reflecting ultrasound. The relative distance between the ultrasonic mirror and the transducer in the longitudinal direction of the probe is changed by a driving unit which may be a wire mounted on the ultrasonic mirror or by a driving unit for causing an attenuation-preventing liquid to flow in and out. Consequently, the position of the focused range of an ultrasonic beam irradiated from the ultrasonic probe in a direction perpendicular thereto can be changed, and a stand-off region can thus be eliminated.

7 Claims, 3 Drawing Sheets

INTRACAVITARY DIAGNOSING APPARATUS EMPLOYING ULTRASOUND

BACKGROUND OF THE INVENTION

This application claims the priority of Japanese Patent Application No. 4-70351 filed on Feb. 20, 1992, which is incorporated herein by reference.

FIELD OF THE INVENTION

The present invention relates to an intracavitary diagnosing apparatus which is inserted into an organism by utilizing the clamp port of an endoscope or the like and displays a tomographic image on a monitor on the basis of the ultrasound emitted from a transducer.

In recent years, intracavitary (ultrasonic) diagnosing apparatus have been known, which invasively display the tomographic image of a desired portion in a body cavity on a monitor by irradiating ultrasound toward the portion to be observed from within the body cavity by an ultrasonic probe inserted into the body cavity. There are some types of intracavitary diagnosing apparatus, including one in which a catheter-like ultrasonic probe having a small diameter is inserted into the body cavity by utilizing the clamp port provided in a presently employed endoscope or electronic endoscope and one which is an ultrasonic probe having a predetermined diameter that can be inserted solely into the body cavity, such as a digestive organ, and displays the image of a relatively large tomographic area.

FIG. 4 schematically illustrates a conventional clamp port inserted type intracavitary diagnosing apparatus (ultrasonic probe). As shown in FIG. 4, a single transducer 2 is provided on the side surface of a distal end portion 1, and an acoustic lens 3 capable of condensing ultrasound is mounted on the transducer 2. The combination of the transducer 2 and the acoustic lens 3 radiate an ultrasonic beam 100 which is characterized by being first condensed and then expanded, as shown in FIG. 4. An excellent focused image can be obtained in the region A. A blurring image is obtained in the region B. A region C represents a stand-off region where no image is obtained. In use, such an ultrasonic probe is inserted into the body cavity from a clamp port 5 provided in an endoscope 4, as shown in FIG. 5. After the probe has been inserted into the body cavity, the operator positions the distal end portion 1 at a desired position while observing the inside of the body cavity from an observation window 6, whereby the tomographic image of that position is obtained.

However, the above-described conventional intracavitary diagnosing apparatus suffers from the problem that it is difficult to observe the tissues which are located near the surface of the body cavity and in contact with the transducer 2 (the acoustic lens 3) because of the presence of the region C (the stand-off region) where no tomographic image can be formed, as shown in FIG. 4. Hence, when it is desired to obtain the image of a portion of an observation portion 8 which is located immediately below the surface thereof, the operator first separates the distal end portion 1 in a direction perpendicular to the direction in which the endoscope 4 is inserted, as shown in FIGS. 5(B) and 5(C), by operating the endoscope 4, adding water (deaerated water), and then moving the distal end portion 1 to a position which ensures that the portion to be observed is located within the focused range A. Thus, the adjustment by the water to be injected and the adjustment of the distance between the desired position and the distal end portion 1 are required, which is troublesome to the operator.

SUMMARY OF THE INVENTION

In view of the above-described problems of the conventional intracavitary diagnosing apparatus, an object of the present invention is to provide an intracavitary diagnosing apparatus which enables a focused range thereof to be changed so that the apparatus can be readily focused to a desired position to be observed, without the need for adjustment by injection of water and/or adjustment of the distance between the desired position and a distal end portion thereof.

To achieve the above object, the present invention provides an intracavitary diagnosing apparatus which comprises a transducer disposed in an ultrasonic probe for outputting ultrasound in the longitudinal direction of a distal end portion of said ultrasonic probe, an ultrasonic mirror disposed in the ultrasonic probe for reflecting the ultrasound output from the transducer to direct the ultrasound into an organ, and a driving means for changing a relative distance between the ultrasonic mirror and the transducer in the longitudinal direction of the probe.

The ultrasonic mirror is provided movable in the longitudinal direction of the probe, and the driving means includes a wire mounted on the ultrasonic mirror. The ultrasonic mirror is driven by the pulling operation of said wire.

The ultrasonic mirror is disposed such that it partitions a liquid introduced into the distal end portion of the ultrasonic probe in the longitudinal direction of the probe, and is movable in the longitudinal direction of the probe. The driving means includes supply passages through which the liquid is supplied to and discharged from front and rear liquid reservoir portions partitioned by the ultrasonic mirror. The ultrasonic mirror is driven by the supply of the liquid into the front and rear liquid reservoir portions.

In the present invention, the ultrasonic mirror is driven in the longitudinal direction of the probe by, for example, automatically or manually operating a wire, whereby the distance between the ultrasonic mirror and the transducer is changed. When the ultrasonic mirror is moved toward the transducer, the focused range shifts to a deeper position. When the ultrasonic mirror is moved away from the transducer, the focused range shifts to a shallow position. Thus, it is possible to display the image of a portion of an observation portion which is located immediately below the surface thereof and which is in contact with the distal end portion of the ultrasonic probe by adjusting the mirror so that it moves away from the transducer.

DETAILED DESCRIPTION OF THE PREFERRED EMBODIMENTS

First Embodiment

Figure 1:
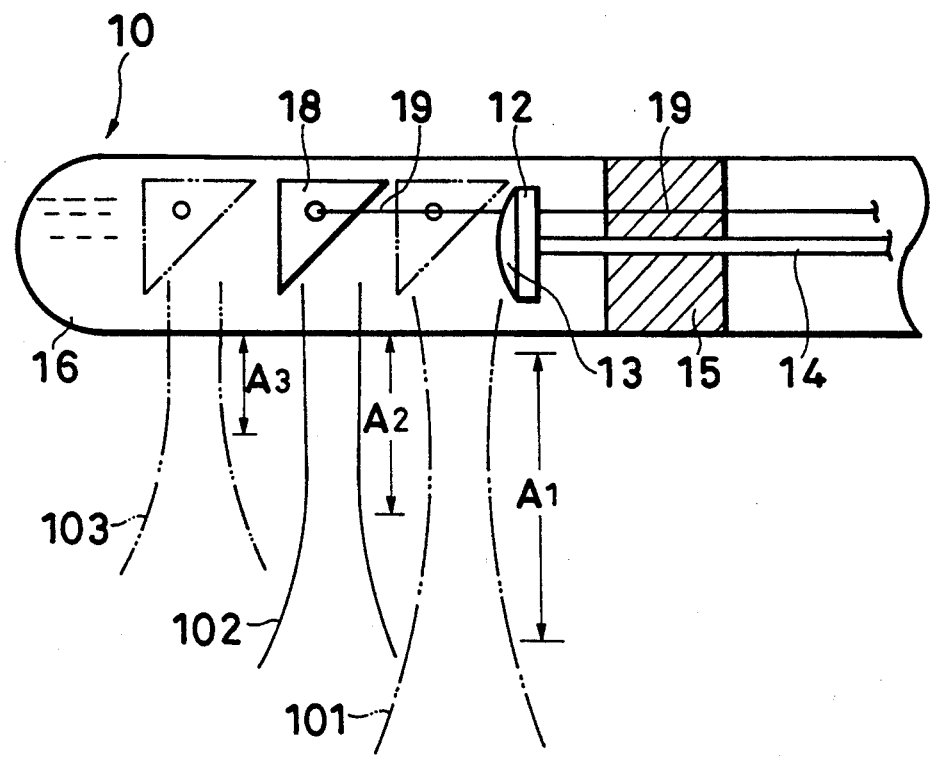
FIG. 1 is a cross sectional view of the distal end portion of an intracavitary diagnosing apparatus (ultrasonic probe), showing a first embodiment of the present invention.

FIG. 1 shows the structure of a distal end portion of a clamp-port-inserted type intracavitary diagnosing apparatus (ultrasonic probe) according to a first embodiment of the present invention. As shown in FIG. 1, a single transducer 12 is provided in a distal end portion 10 in a direction perpendicular to the longitudinal direction of the probe, and an acoustic lens 13 is mounted in the transducer 12 to condense an ultrasonic beam. A signal line 14 extends to supply a driving signal. The distal end portion 10 is partitioned by a partitioning plate 15. The separated portion of the distal end portion 10 is filled with a liquid 16 to prevent attenuation of the ultrasound. A prism-like ultrasonic mirror 18 is immersed in the liquid 16 in front of the transducer 12. A wire 19 is connected to the ultrasonic mirror 18. The wire 19 extends to a rear end portion of the ultrasonic probe so that it can be manually operated at the rear end portion. The wire 19 may also be driven automatically by means of, for example, a motor.

In the above-described structure, a condensed ultrasonic beam is emitted by driving the transducer 12. The irradiated ultrasonic beam is reflected by the ultrasonic mirror 18, and thereby directed toward a portion to be observed from the lower side of the endoscope, as viewed in FIG. 1. At that time, the operator can move the ultrasonic mirror 18 in the longitudinal direction of the probe by pulling or pushing the wire 19. Consequently, when the ultrasonic mirror 18 is close to the transducer 12 at a position indicated by the dot-dot-dashed line, as shown in FIG. 1, an ultrasonic beam 101 having a focused range A1 can be obtained. When the ultrasonic mirror 18 is at a position indicated by the solid line, an ultrasonic beam 102 having a focused range A2 can be obtained. When the ultrasonic mirror 18 is separated from the transducer 12 to a position indicated by the dot-dot-dashed line, an ultrasonic beam 103 having a focused range A3 can be obtained.

Figure 4:
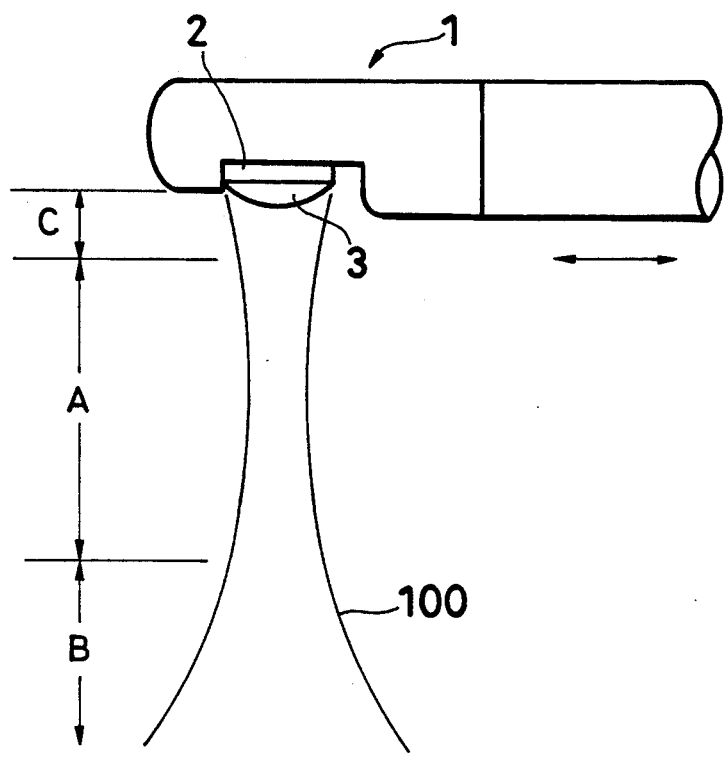
FIG. 4 is a side elevational view of the distal end portion of a conventional ultrasonic probe.
Figure 5:
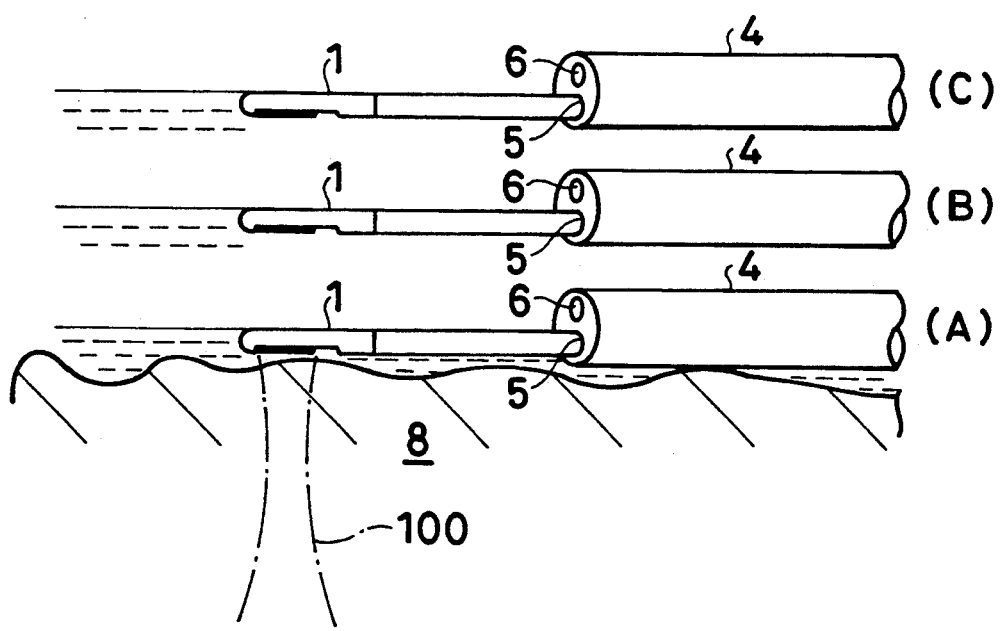
FIG. 5 illustrates how the conventional ultrasonic probe is used.

In this embodiment, the position of a focused range A (the depth) on the tomographic plane can be freely changed by moving the ultrasonic mirror 18 in the longitudinal direction of the probe, as described above. Therefore, it is possible to eliminate the (stand-off) region (region C shown in FIG. 4) where no image can be formed conventionally, and thereby readily obtain the tomographic image of the portion of the observation portion which is located immediately below the surface thereof. In other words, the operation of separating the ultrasonic probe or the endoscope from the surface of the observation portion in order to locate the desired observation portion within the focused range A, described in connection with FIG. 5, is unnecessary, and the desired observation position can be located within the focused range A only by moving the ultrasonic mirror 18 to obtain the tomographic image thereof. Thus, injection of water can also be eliminated.

Second Embodiment

Figure 2:
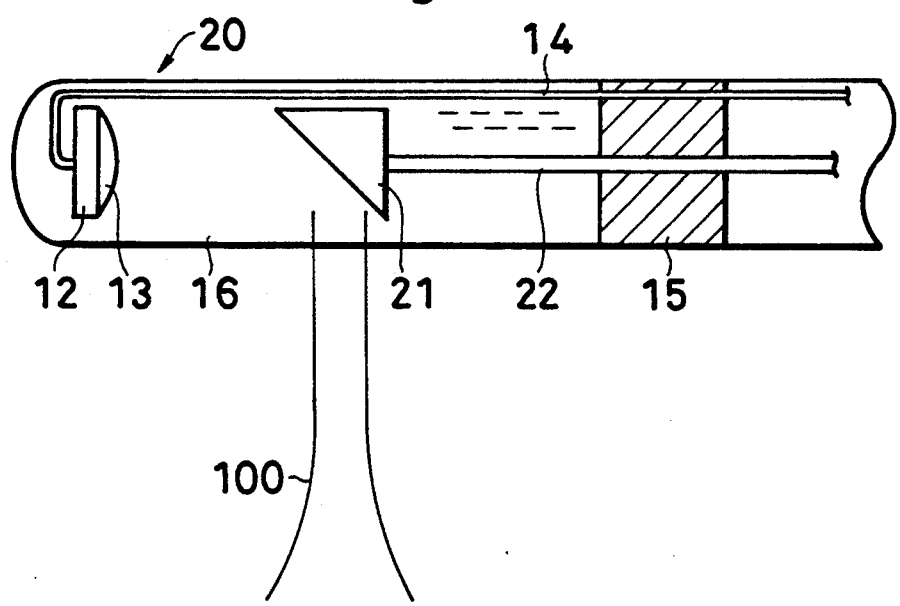
FIG. 2 is a cross-sectional view of the distal end portion of a second embodiment according to the present invention.

FIG. 2 shows the structure of the ultrasonic probe according to a second embodiment of the present invention. This embodiment differs from the embodiment shown in FIG. 1 in the position of the transducer and that of the ultrasonic mirror. As shown in FIG. 2, the transducer 12 with the acoustic lens 13 mounted thereon is provided at the most distal end portion of a distal end portion 20 and an ultrasonic mirror 21 is disposed in the liquid 16 filling the distal end portion 20 in such a manner that it faces the radiating surface of the transducer 12. A wire 22 is connected to a central portion of the rear end surface of the ultrasonic mirror 21 so that the ultrasonic mirror 21 can be moved back and forth and rotated by a predetermined angle through the wire 22.

As in the case of the first embodiment, the focused range A of the ultrasound radiating from the side surface of the probe can be adjusted by driving the ultrasonic mirror 21 by the wire 22 in the longitudinal direction of the probe in the second embodiment. Furthermore, the tomographic plane where the ultrasound is transmitted and received can be transformed by rotating the wire 22 a predetermined angle. Therefore, the tomographic position in the direction of rotation about the axis of the ultrasonic probe can be adjusted without rotating the ultrasonic probe itself.

Third Embodiment

Figure 3:
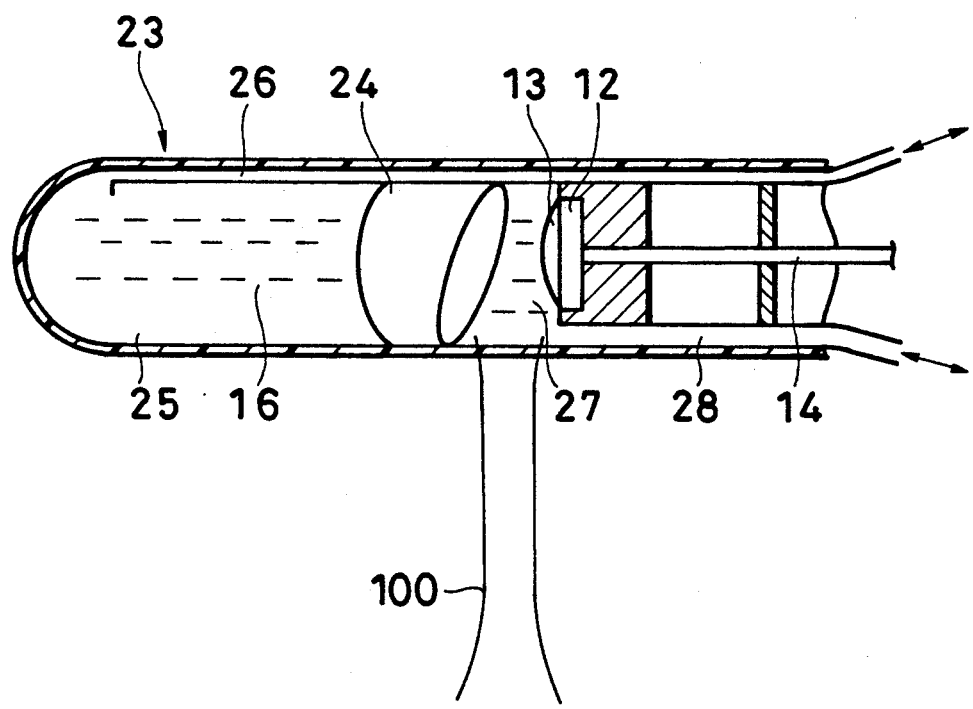
FIG. 3 is a cross-sectional view of the distal end portion of a third embodiment according to the present invention.

FIG. 3 shows the structure of the ultrasonic probe according to a third embodiment of the present invention. In the third embodiment, driving of the ultrasonic mirror is performed by controlling flow-in and flow-out of the attenuation-preventing liquid. In FIG. 3, an ultrasonic mirror 24 has a column-like shape and a size which enables it to slide while it is making contact with the inner peripheral surface of a distal end portion 23. A first supply passage 26 is formed on the front side of the ultrasonic mirror 24 in such a manner that it communicates with a liquid reservoir portion 25 of the liquid 16, and a second supply passage 28 is provided on the rear side of the ultrasonic mirror 24 between the transducer 12 and the mirror 24 in such a manner that it communicates with a liquid reservoir portion 27. Thus, the ultrasonic mirror 24 can be moved toward the transducer 12 by causing the liquid 16 to flow in through the first supply passage 26 while permitting it to flow out from the second supply passage 28. In contrast, the ultrasonic mirror 24 can be moved away from the transducer 12 by controlling flow-in and flow-out of the liquid in reverse directions.

In the third embodiment, the relative distance between the ultrasonic mirror 24 and the transducer 12 can be changed by utilizing the liquid 16 introduced in order to prevent attenuation of the ultrasound without using a wire, whereby the position of the focused range A can be changed, as in the case of the above-described embodiments.

The above embodiments are arranged such that the ultrasonic mirrors 18, 21 and 24 are driven. However, the relative distance between the ultrasonic mirrors and the transducer 12 may be changed by driving the transducer 12. Furthermore, although the clamp-port inserted type ultrasonic probe has been described in the above embodiments, the present invention can also be applied to an intracavitary ultrasonic diagnosing apparatus which is solely inserted into the body cavity, such as an esophagus probe.

As will be understood from the foregoing description, in the present invention, since the relative distance between the ultrasonic mirror and the transducer in the longitudinal direction of the probe is changed by means of a driving means which is a wire mounted on the ultrasonic mirror or by a driving means in which an attenuation-preventing liquid is caused to flow in and out, the position of the focused range of the ultrasonic beam irradiated in a direction perpendicular to the ultrasonic probe can be changed so as to enable the probe to be focused to a desired portion to be observed. Thus, the adjustment of the water to be injected and the adjustment of the distance between the desired observation portion and the distal end portion, which would be required when the image of the tomographic plane located immediately below the surface of the portion to be observed is displayed, can be eliminated, and positioning of the probe can readily be made.

What is claimed is:

1. An intracavitary diagnosing apparatus comprising:
   a transducer disposed in an ultrasonic probe for outputting ultrasound in a longitudinal direction of a distal end portion of said ultrasonic probe;
   an ultrasonic mirror disposed in said ultrasonic probe on the distal end side of said transducer for reflecting the ultrasound output from said transducer to direct the ultrasound as a focused ultrasonic beam into an organ; and
   a driving means for moving said ultrasonic mirror and changing a relative distance between said ultrasonic mirror and said transducer in the longitudinal direction of said probe, thereby changing the position of the focused range of the ultrasonic beam, said driving means including a wire mounted on said ultrasonic mirror, whereby said ultrasonic mirror can be driven by the pulling operation of said wire.

2. An intracavitary diagnosing apparatus employing ultrasound according to claim 1, wherein said driving means moves said transducer.

3. An intracavitary diagnosing apparatus according to claim 1, wherein said ultrasonic probe comprises a catheter-like probe, and said apparatus being a combination of said ultrasonic probe and an internal imaging device.

4. An intracavitary diagnosing apparatus comprising:
   a transducer disposed in an ultrasonic probe for outputting ultrasound in a longitudinal direction of a distal end portion of said ultrasonic probe;
   an ultrasonic mirror disposed in said ultrasonic probe for reflecting the ultrasound output from said transducer to direct the ultrasound as a focused ultrasonic beam into an organ; said ultrasonic mirror being rotatable and movable in the longitudinal direction of said probe;
   said transducer being disposed on the distal end side of said ultrasonic mirror;
   a driving means for moving said ultrasonic mirror and changing a relative distance between said ultrasonic mirror and said transducer in the longitudinal direction of said probe thereby changing the position of the focused range of the ultrasonic beam, said driving means including a wire mounted on said ultrasonic mirror, whereby said ultrasonic mirror can be driven by both the pulling operation of said wire to move the ultrasonic mirror back and forth in the longitudinal direction of the probe and by rotating the wire to rotate the ultrasonic mirror to adjust the tomographic plane where the ultrasound is transmitted and received.

5. An intracavitary diagnosing apparatus comprising:
   a transducer disposed in an ultrasonic probe for outputting ultrasound in a longitudinal direction of a distal end portion of said ultrasonic probe;
   a ultrasonic mirror disposed in said ultrasonic probe for reflecting the ultrasound output from said transducer to direct ultrasound into an organ;
   a driving means for moving said ultrasonic mirror in a longitudinal direction in the probe and changing a relative distance between said ultrasound mirror and said transducer in the longitudinal direction of said probe;
   said ultrasonic mirror being disposed such that it partitions a liquid introduced into the distal end portion of said ultrasonic probe in the longitudinal direction of said probe,
   said driving means comprising supply passages through which the liquid is supplied to and discharged from front and rear liquid reservoir portions partitioned by said ultrasonic mirror, said ultrasonic mirror being driven by the supply of the liquid into said front and rear reservoir portions.

6. An intracavitary diagnosing apparatus employing ultrasound according to claim 5, wherein said ultrasonic mirror is disposed on the distal end side of said transducer.

7. An intracavitary diagnosing apparatus employing ultrasound according to claim 5, wherein said transducer is disposed on the distal end side of the ultrasonic mirror.

* * * * *